(12) United States Patent
Laskoski et al.

(10) Patent No.: US 7,723,420 B2
(45) Date of Patent: May 25, 2010

(54) SYNTHESIS AND POLYMERIZATION OF OLIGOMERIC DIVINYL-TERMINATED AROMATIC ETHER-CONTAINING RESINS

(75) Inventors: Matthew Laskoski, Springfield, VA (US); Teddy M Keller, Fairfax Station, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 12/179,664

(22) Filed: Jul. 25, 2008

(65) Prior Publication Data

US 2010/0022693 A1    Jan. 28, 2010

(51) Int. Cl.
| | |
|---|---|
| C08K 3/18 | (2006.01) |
| C08K 3/22 | (2006.01) |
| C08K 3/34 | (2006.01) |
| C08K 9/04 | (2006.01) |
| C08G 77/00 | (2006.01) |
| C08G 77/04 | (2006.01) |
| C08G 65/38 | (2006.01) |
| C08G 63/78 | (2006.01) |
| C08G 63/87 | (2006.01) |
| C08G 61/00 | (2006.01) |
| C08G 77/20 | (2006.01) |
| C08C 1/14 | (2006.01) |

(52) U.S. Cl. ............ 524/430; 528/10; 528/29; 528/219; 528/205; 528/397; 528/32; 528/488; 524/445; 977/742

(58) Field of Classification Search ........... 528/29, 528/32

See application file for complete search history.

(56) References Cited

U.S. PATENT DOCUMENTS

| | | | | |
|---|---|---|---|---|
| 3,536,657 A | * | 10/1970 | Barth et al. ............ | 524/540 |
| 3,857,825 A | * | 12/1974 | Streck et al. ........... | 526/128 |
| 4,183,874 A | * | 1/1980 | Fan et al. ............. | 525/100 |
| H521 H | * | 9/1988 | Fan .................... | 525/391 |
| 5,969,072 A | | 10/1999 | Keller et al. | |
| 5,981,678 A | | 11/1999 | Keller et al. | |
| 6,225,247 B1 | | 5/2001 | Keller et al. | |
| 7,153,921 B2 | | 12/2006 | Keller et al. | |
| 7,238,766 B2 | | 7/2007 | Keller et al. | |
| 2005/0137307 A1 | * | 6/2005 | Yeager ................. | 524/425 |
| 2005/0171233 A1 | * | 8/2005 | Bublewitz et al. ........ | 523/116 |
| 2006/0041086 A1 | * | 2/2006 | Birsak et al. ........... | 525/391 |
| 2006/0235195 A1 | * | 10/2006 | Keller et al. ........... | 528/367 |

OTHER PUBLICATIONS

Laskoski, M., and Keller, T.M. "Synthesis and properties of an oligomeric divinyl-terminated aromatic ether containing resin." Journal of Materials Chemistry, vol. 19, p. 3307-3310, Mar. 31, 2009.*
Laskoski et at., "Divinylsilane-Terminated Aromatic Ether-Aromatic Ketone-Containing Compounds" U.S. Appl. No. 12/020,623, filed Jan. 28, 2008.

* cited by examiner

*Primary Examiner*—Vasu Jagannathan
*Assistant Examiner*—Anthony H Sheh
(74) *Attorney, Agent, or Firm*—Amy L. Ressing; Joseph T. Grunkemeyer

(57) ABSTRACT

An oligomer having the formula:

$$CH_2=CH-\underset{\underset{CH_3}{|}}{\overset{\overset{CH_3}{|}}{Si}}-(O)_m-Ar^2-(O-Ar^1-O-Ar^2)_n-(O)_m-\underset{\underset{CH_3}{|}}{\overset{\overset{CH_3}{|}}{Si}}-CH=CH_2.$$

$Ar^1$ and $Ar^2$ are each an aromatic group or a bisphenol residue. At least one of $Ar^1$ and $Ar^2$ is the aromatic group. The value of m is zero or one, and n is a positive integer. A polymer made by reacting the above oligomer with a crosslinker having at least two silyl hydrogen atoms. A method of: reacting a compound having the formula:

$$T-Ar^2-(O-Ar^1-O-Ar^2)_n-T$$

with vinyl(dimethylchloro)silane to form the above oligomer. T is —OH, —Br, or —I.

24 Claims, No Drawings

SYNTHESIS AND POLYMERIZATION OF OLIGOMERIC DIVINYL-TERMINATED AROMATIC ETHER-CONTAINING RESINS

FIELD OF THE INVENTION

The invention is generally related to divinyl-terminated aromatic ether-containing resins.

DESCRIPTION OF RELATED ART

The rapid advancement of modern technology in recent years has increasingly demanded new high performance materials for use in a wide variety of engineering applications and under unusual service conditions. High temperature elastomers that have thermal, thermo-oxidative and hydrolytic stability above 300° C. (572° F.), and maintain flexibility to well below ambient temperature are in demand for numerous marine and aerospace applications. High temperature, tough elastomers are needed for high voltage electrical cables for advanced ships. Such elastomers are highly desirable for components in high flying airplanes and space vehicles, which experience extreme variations of temperatures from as low as −50° C. to as high as 300-350° C. High temperature coatings are also useful for electronic devices. Such elastomers or networked systems would also be desirable for high temperature integral fuel tank sealants, which require long lasting elastomers (up to 10,000 hours) for use from −60° C. to 400° C. without swelling on contact with jet fuels but with excellent adhesion and inertness toward metallic substrates.

SUMMARY OF THE INVENTION

The invention comprises an oligomer having the formula shown in Eq. (1).

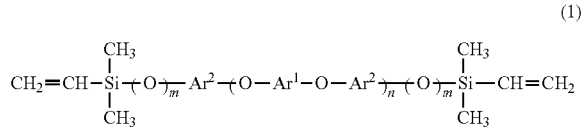

(1)

$Ar^1$ and $Ar^2$ are each selected from an aromatic group and a bisphenol residue. At least one of $Ar^1$ and $Ar^2$ is the aromatic group. The value of m is zero or one, and n is a positive integer.

The invention further comprises a polymer made by reacting the above oligomer with a crosslinker having at least two silyl hydrogen atoms.

The invention further comprises a method comprising: reacting a compound having the formula in Eq. (2) with vinyl(dimethylchloro)silane to form the above oligomer. T is —OH, —Br, or —I.

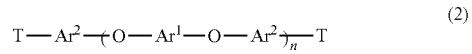

(2)

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail. All chemical groups, such as aromatic groups, include unsubstituted and substituted forms of the group.

Disclosed herein is the synthesis and polymerization of divinyl-terminated multiple aromatic ether-containing oligomeric resins, which are precursors to novel high temperature elastomers and coatings. As synthesized in two steps, the resins may be transparent liquids. The oligomeric resins can be converted to high temperature elastomers at room temperature (slow) or at temperatures in excess of 100° C. High temperature, tough elastomers that can be processed under ambient conditions do not exist today containing oligomeric multiple aromatic ether units between the polymerization centers (vinyl). These vinyl terminated units are interconnected by aromatic ether moieties with varying lengths, which will affect the physical properties of the elastomeric thermosets. Since the novel divinyl terminated oligomers may be viscous liquids and may be soluble in most organic solvents, they can be fabricated into shaped elastomeric components or can be deposited as film or onto fibrous materials as coatings in the presence of a curing additive. Polymerization can be achieved under ambient condition by hydrosilation reactions, which involve the interaction of a curing additive containing multiple —SiH units with the vinyl terminated units in the presence of a catalyst. This is the first known reaction of a resin containing multiple aromatic ether-vinyl terminated units with a compounds containing —SiH units to form networked elastomeric polymers. The incorporation of the aromatic units within the backbone enhances the stiffness, mechanical, thermal, and oxidative properties of the networked polymers fabricated from the oligomeric resins.

The multiple aromatic ether-containing divinyl terminated oligomeric resins can be polymerized through the terminated vinyl groups to afford high temperature, flame resistant networked or crosslinked elastomers. Depending on the amount of curing additive and the curing temperature, soft-to-hard elastomers (rubbers) can be obtained from the oligomers. The elastomeric properties can also be readily controlled by the distance between the curing or crosslinked sites. Polymeric coatings formulated from the oligomeric aromatic ether-containing divinyl terminated resins may have outstanding thermo-oxidative and flammability properties for potential military (ship, submarine, aerospace) and domestic applications and may withstand continuous high temperatures (300-375° C.) in oxidative environments such as air for extended periods. The use of low molecular weight precursor resins to obtain thermosetting polymeric materials with high thermo-oxidative properties is often advantageous from a processing standpoint.

Presently disclosed materials may be used as high temperature elastomers and flame resistant composites and may address composite processability issues based on cost effective manufacturing techniques such as resin transfer molding (RTM), resin infusion molding, and filament winding. Incorporation of aromatic units within the backbone may enhance the flammability resistance and thermo-oxidative properties while retaining low temperature processability. The liquid, low viscosity resin may enable the deposition of a coating onto a substrate by typical coating procedures.

Scheme 1 shows a general procedure for the synthesis of 1 and 2 and conversion to elastomer 3. During the synthesis of oligomeric 1, the average molecular weight is dependent on the ratios of reactants, bisphenol and dibromoaromatic compound, used. The length of the spacer between the terminal divinyl groups of 2 can be varied by changing the ratio between bisphenol (excess) and the dibromoaromatic compound. Any bisphenol and dibromo- or diiodoaromatic compound can be used in the synthesis. Scheme 2 show the formation of hydroxyl-terminated 1 from reaction of 1,3-dibromobenzene and bisphenol A (excess). Further reaction of 1 with chlorodimethylvinylsilane afforded the divinyl terminated oligomers 2 in 91-95% yields. Oligomers 2 are readily soluble in common organic solvents such as toluene, DMF, acetone, methylene chloride, ether, and chloroform.

The structure of the oligomers 2 was confirmed by IR and $^1$H-NMR spectroscopy. Oligomeric divinyl resins 2 may be light yellow liquids, which can enhance their importance for coating applications. Changing any of the reactants and variables mentioned above can lead to elastomeric thermoset 3 of different properties. Reaction of 2 with any compound (curing additive) containing multiple SiH units can lead to transparent amber color thermosetting elastomer 3. Thus, it is possible to tailor the cured polymer 3 according to specific needs. Three curing additives are shown in Scheme 3. The crosslinked polymer 3 can exhibit outstanding thermal and oxidative properties to about 400° C.

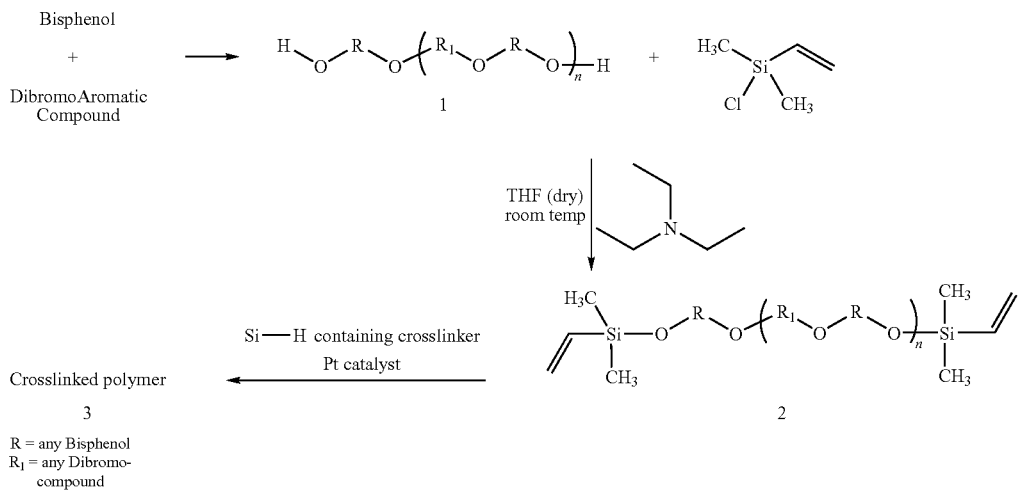

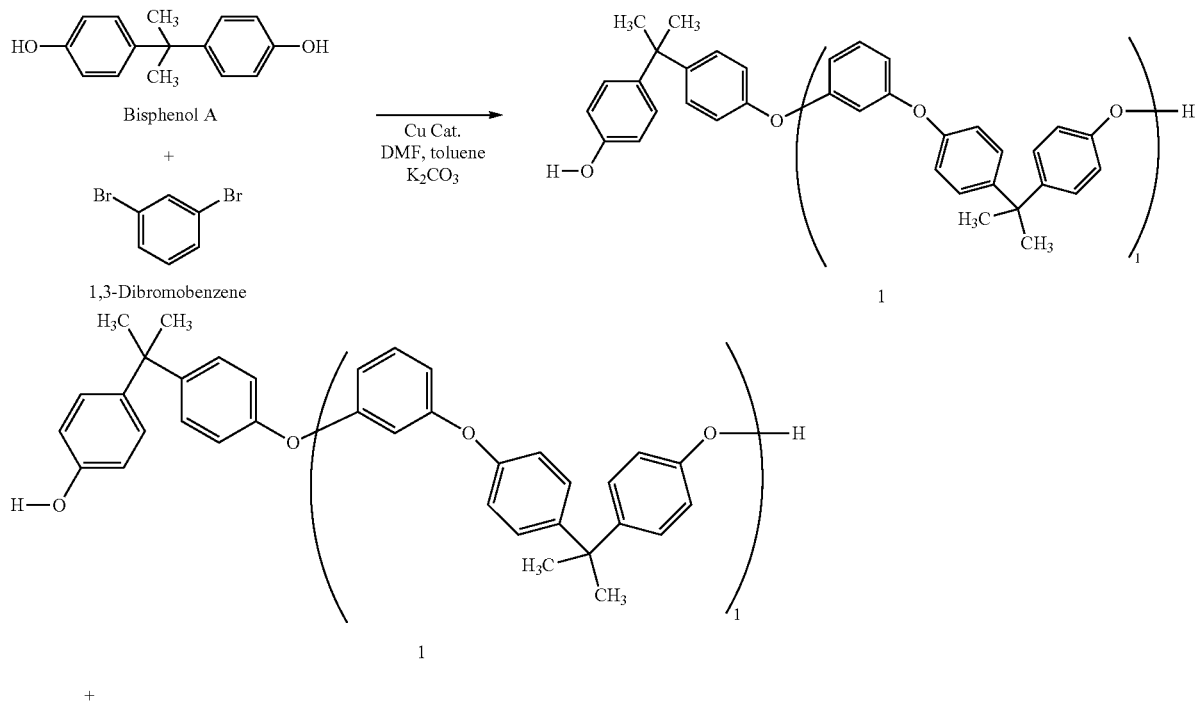

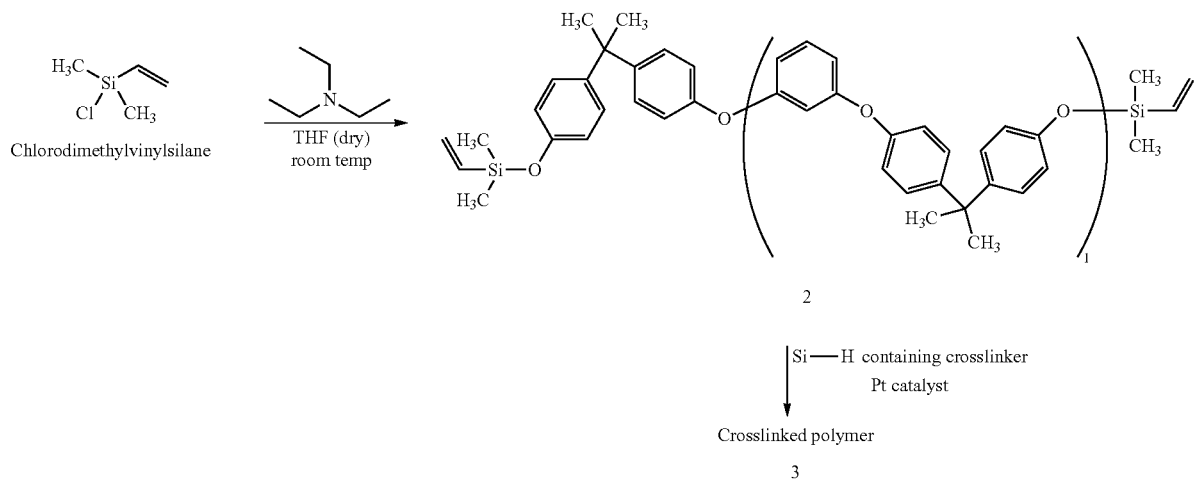

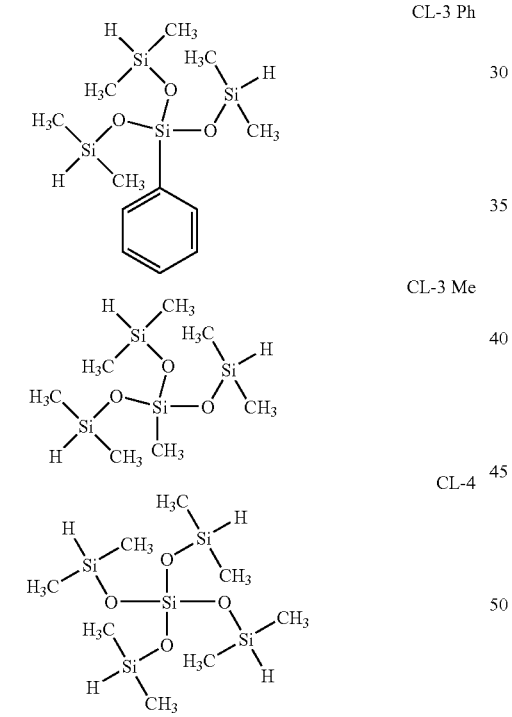

Generally, the compound of Eq. (2) may be made by any reaction of dibromoaromatic or diiodoaromatic with a bisphenol or a dihydroxyaromatic. The aromatic groups may be any divalent substituted or unsubstituted, fused or non-fused aromatic groups including, but not limited to, phenylene and naphthylene. The term "bisphenol residue" refers to the moiety incorporated into the oligomer with the hydrogen atoms of the hydroxyl groups are removed in the reaction with the dibromo- or diiodoaromatic. When the bisphenol or dihydroxyaromatic is in excess, the value of m (in Eq. (1)) is 1. When, for example, the dibromobenzene or diiodobenzene is in excess, the value of m is zero. When the ratio of the two reactants is 2:1, the average value of n is 1. The value of n increases as the ratio approaches 1:1. The compound may then be reacted with vinyl(dimethylchlorosilane) to form the oligomer of Eq. (1). Examples of oligomers are shown in Eqs. (3)-(5). X may be H or F.

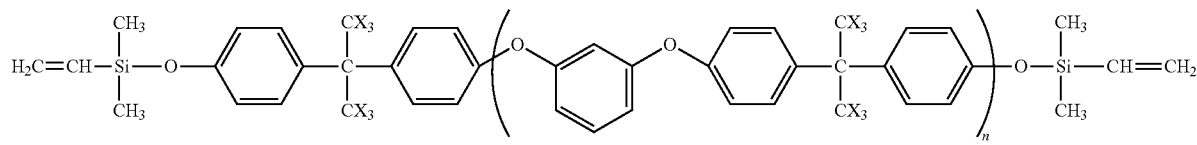

(3)

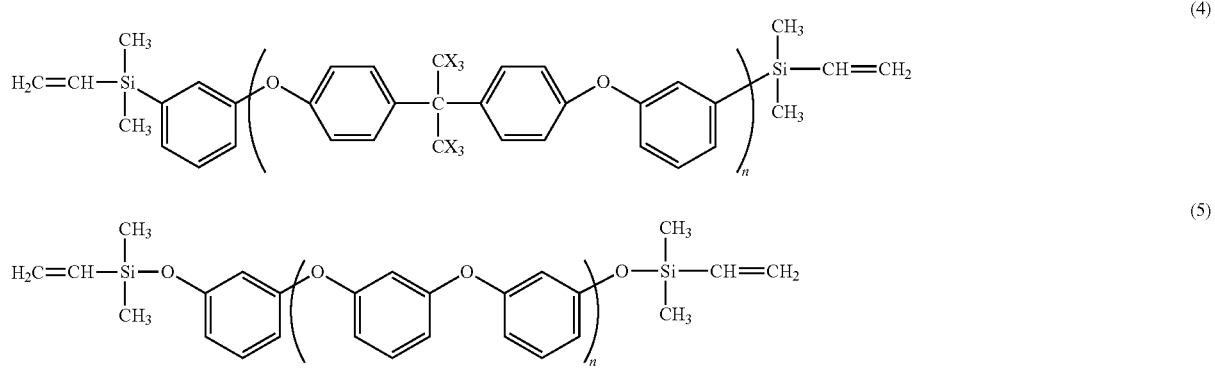

The oligomer may then be reacted with a crosslinker having at least two silyl hydrogens. This reaction is described in, for example, U.S. Pat. Nos. 5,969,072; 5,981,678; 6,225,247; 7,153,921; and 7,238,766. (All publications and patent documents referenced throughout this application are incorporated herein by reference.) Suitable crosslinkers include, but are not limited to, tetrakis(dimethylsiloxy)silane, bis[(p-dimethylsilyl)phenyl]ether, diphenylsilane, 1,1,3,3,5,5,7,7-octamethyltetrasiloxane, 1,1,3,3-tetramethyldisiloxane, phenyl tris(dimethylsiloxy)silane, methyl tris(dimethylsiloxy)silane, and a hydride terminated polydimethylsiloxane. An example of the crosslinked portion of the polymer is shown in Eq. (6). Reacting the oligomer with the crosslinker may also occur in the presence of carbon nanotubes, a clay, carbon nanofibers, a metal oxide, or microballoons. Microballoons are micron sized hollow glass beads.

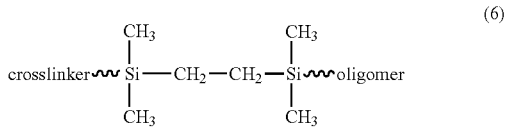

(6)

Disclosed herein are low molecular weight multiple aromatic ether hydroxyl terminated compounds 1 used in the preparation of oligomeric divinyl terminated monomer 2. The oligomeric 2 was converted to crosslinked polymer 3 under thermal conditions and in the presence of a curing additive. Upon addition of the curing additive at room temperature, the vinyl groups slowly commenced to react. Processability to the crosslinked elastomers 3 is controlled as a function of the exposure temperature. Thus, depending on the curing conditions, thermal parameters, and distance between the terminal vinyl units, high temperature thermosetting soft-to-hard rubber compositions can be obtained. Regardless of the curing conditions, the oligomeric vinyl terminated resin 2 can be converted to thermosetting elastomers 3 or can be injected into a fiber-reinforced preform for the fabrication of complex shaped composite components. Various fillers can also be incorporated into the resin 2 and cured to shaped structural components. The elastomeric polymer 3 can exhibit thermal and oxidative stability to about 400° C. before any significant weight loss. The overall physical properties can be tailored by varying the bisphenol and dibromoaromatic reactants in the synthesis of 2. Regardless of whether the cured polymer is a soft or hard elastomer (rubber), amber shaped film or solids, which enhance their importance for electronic, electrical, and structural applications, may be formed. By controlling the reactivity of the catalyst in the curing reaction, the viscosity of the polymerization system can be easily controlled for extended periods yielding a processing window, which may be advantageous for the fabrication of complex composite components and device coatings. Due to the thermal and oxidative stability of thermoset or network polymers 3 cured to temperatures in excess of 350° C., the materials have potential for a variety of applications including the fabrication of advanced composite components (ship, aerospace, and marine) by conventional prepreg consolidation, RTM, injection molding, and filament winding and as a coating for electronic devices and for electrical insulator for high voltage cables.

The synthesis of precursor resins 2 can be a simple two step reaction leading initially to 1 in high yield. Reaction of 1 with chlorodimethylvinylsilane can afford 2 quantitatively. The flexible aromatic ether units can contribute to the processability (liquid) of the oligomeric vinyl terminated resin 2 and may be responsible for the high temperature stability of elastomers 3 due to their own inherent thermal stability. By controlling the ratio of reactants, bisphenol and dibromoaromatic compound, in the synthesis of compound 1, different percentages of vinyl and aromatic ether units can be obtained in the resulting oligomeric compound 2. A combination of reactants can be found to produce a polymer 3 tailored for a particular application.

Having described the invention, the following examples are given to illustrate specific applications of the invention. These specific examples are not intended to limit the scope of the invention described in this application.

EXAMPLE 1

Synthesis of 2:1 hydroxy terminated oligomer based on bisphenol A and 1,3-dibromobenzene—To a 100 mL three neck flask fitted with a thermometer, a Dean-Stark trap with condenser, and nitrogen inlet was added bisphenol A (10.0 g, 43.8 mmol), 1,3-dibromobenzene (2.64 mL, 5.16 g, 21.9 mmol), 1,10-phenanthroline (350 mg, 1.94 mmol), and N,N-dimethylformamide (50 mL). The resulting mixture was degassed with nitrogen for 10 min, followed by the addition of copper (I) bromide (420 mg, 2.94 mmol) and $Cs_2CO_3$ (7.80 g, 23.9 mmol). After filling the Dean-Stark trap with toluene and adding 5 mL to the reaction flask, the mixture was heated to reflux at 145° C. for 1 hr. The water formed in the reaction was removed by azeotropic distillation and at this time an additional portion of $K_2CO_3$ (15.1 g, 111 mmol) was added. The mixture was refluxed for 9-12 hr until no more water was observed being collected in the Dean-Stark trap. The remaining toluene was then removed by distillation and the reaction mixture cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by addition of 200 mL of 10% NaOH solution. The mixture was then extracted with ether (2×100 mL) to remove impurities and the water layer was made acidic by the addition of 100 mL of 2 M HCl solution. The aqueous solution was again extracted with ether (2×100 mL) and the ether layers were combined. Carbon black (2 g) was added and the ether filtered through a short plug of silica gel to remove any insoluble components. The solvent was removed and the oil was vacuum dried to yield the analytically pure 2:1 hydroxy terminated oligomer (10.3 g, 92%) as an amber solid.

EXAMPLE 2

Synthesis of 2:1 oligomeric vinyl silane terminated resin based on bisphenol A and 1,3-dibromobenzene—To a 100 mL three-necked flask fitted with a thermometer, a Dean-Stark trap with condenser, and a nitrogen inlet were added the 2:1 bisphenol A/1,3-dibromobenzene based hydroxyl terminated aromatic ether oligomer (2.00 g, 3.77 mmol), triethylamine (1.16 ml, 8.32 mmol), and anhydrous tetrahydrofuran (25 mL). The reaction mixture was cooled by means of an ice bath and vinyl(dimethylchloro)silane (1.09 mL, 7.70 mmol) added dropwise. The resulting mixture was stirred for 1 h. The mixture was poured into water and extracted with diethyl ether. The solvent was removed in vacuo and the resulting oil was dissolved in 1:1 methylene chloride:hexane and filtered through a silica plug. The solvent was removed in vacuo and the clear oil was vacuum dried to yield the 2:1 oligomeric vinyl silane terminated resin (2.47 g, 98%). IR [cm$^{-1}$]: δ 3052 (C=CH), 2967 (CH$_3$), 1593 (C=C), 1500 (aromatic), 1242 (C—O), 1171 (C—O), 834 (aromatic).

EXAMPLE 3

Catalytic hydrosilylation reaction with 2:1 oligomeric vinyl silane terminated resin based on bisphenol A and 1,3-dibromobenzene and tetrakis(dimethylsiloxy) silane (2:1 ratio)—A mixture formulated from the 2:1 oligomeric vinyl silane terminated resin (0.40 g) of Example 2 and tetrakis (dimethylsiloxy)silane (0.08 mL) was dissolved in 1 mL of dry toluene. While stirring, 7 μL of 2-2.5% platinum-vinylmethylsiloxane complex in xylene solution was added. The mixture was transferred to a silicone mold and was allowed to gel at room temperature (12 h). The sample was post cured above 100° C. to completely cure the resin. The result was a transparent elastomeric sample, which had good thermal and oxidative stability and retained >40% weight after heating under air to 1000° C.

EXAMPLE 4

Catalytic hydrosilylation reaction with 2:1 oligomeric vinyl silane terminated resin based on bisphenol A and 1,3-dibromobenzene and bis[(p-dimethylsilyl)phenyl]ether (2.5:1 ratio)—A mixture formulated from the 2:1 oligomeric vinyl silane terminated resin (0.35 g) of Example 2 and bis [(p-dimethylsilyl)phenyl]ether (0.05 g) was dissolved in 1 mL of dry toluene. While stirring, 10 μL of 2-2.5% platinum-vinylmethylsiloxane complex in xylene solution was added. The mixture was transferred to a silicone mold and allowed to gel at room temperature (12 h). The sample was post cured above 100° C. to completely cure the resin. The result was a transparent elastomeric sample, which had good thermal and oxidative stability and retained >40% weight after heating under air to 1000° C.

EXAMPLE 5

Catalytic hydrosilylation reaction with 2:1 oligomeric vinyl silane terminated resin based on bisphenol A and 1,3-dibromobenzene and diphenylsilane (1:1 ratio)—A mixture formulated from the 2:1 oligomeric vinyl silane terminated resin (0.55 g) of Example 2 and diphenylsilane (0.13 g) was dissolved in 1 mL of dry toluene. While stirring, 10 μL of 2-2.5% platinum-vinylmethylsiloxane complex in xylene solution was added. The mixture was transferred to a silicone mold and allowed to gel at room temperature (2 h). The sample was post cured above 100° C. to completely cure the resin. The result was a transparent elastomeric sample, which had good thermal and oxidative stability and retained >40% weight after heating under air to 1000° C.

EXAMPLE 6

Catalytic hydrosilylation reaction with 2:1 oligomeric vinyl silane terminated resin based on bisphenol A and 1,3-dibromobenzene and 1,1,3,3,5,5,7,7-octamethyltetrasiloxane (1:1 ratio)—A mixture formulated from the 2:1 oligomeric vinyl silane terminated resin (0.50 g) of Example 2 and 1 μl, 3,3,5,5,7,7-octamethyltetrasiloxane (0.20 g) was dissolved in 1 mL of dry toluene. While stirring, 20 μL of 2-2.5% platinum-vinylmethylsiloxane complex in xylene solution was added. The mixture was transferred to a silicone mold and allowed to gel at room temperature (2 h). The sample was post cured above 100° C. to completely cure the resin. The result was a transparent elastomeric sample, which had good thermal and oxidative stability and retained >40% weight after heating under air to 1000° C.

EXAMPLE 7

Catalytic hydrosilylation reaction with 2:1 oligomeric vinyl silane terminated resin based on bisphenol A and 1,3-dibromobenzene and tetrakis(dimethylsiloxy)silane (2.5:1 ratio)—A mixture formulated from the 2:1 oligomeric vinyl silane terminated resin (0.40 g) of Example 2 and tetrakis (dimethylsiloxy)silane (0.06 mL) was dissolved in 1 mL of dry toluene. While stirring, 15 μL of 2-2.5% platinum-vinylmethylsiloxane complex in xylene solution was added. The mixture was transferred to a silicone mold and allowed to gel at room temperature (5 min). The sample was post cured above 100° C. to completely cure the resin. The result was a transparent elastomeric sample, which had good thermal and oxidative stability and retained >40% weight after heating under air to 1000° C.

EXAMPLE 8

Catalytic hydrosilylation reaction with 2:1 oligomeric vinyl silane terminated resin based on bisphenol A and 1,3-dibromobenzene and 1,1,3,3-tetramethyldisiloxane (2.5:1 ratio)—A mixture formulated from the 2:1 oligomeric vinyl silane terminated resin (0.80 g) of Example 2 and 1,1,3,3-tetramethyldisiloxane (0.15 mL) was dissolved in 1 mL of dry toluene. While stirring, 25 μL of 2-2.5% platinum-vinylmethylsiloxane complex in xylene solution was added. The mixture was transferred to a silicone mold and allowed to gel at room temperature (1 h). The sample was post cured above 100° C. to completely cure the resin. The result was a transparent elastomeric sample, which had good thermal and oxidative stability and retained >40% weight after heating under air to 1000° C.

EXAMPLE 9

Synthesis of 2:1 hydroxy terminated oligomer based on Bisphenol A6F and 1,3-dibromobenzene—To a 100 mL three neck flask fitted with a thermometer, a Dean-Stark trap with condenser, and nitrogen inlet was added bisphenol A6F (14.7 g, 43.8 mmol), 1,3-dibromobenzene (2.64 mL, 5.16 g, 21.9 mmol), 1,10-phenanthroline (350 mg, 1.94 mmol), and N,N-dimethylformamide (50 mL). The resulting mixture was degassed with nitrogen for 10 min, followed by the addition of copper (I) bromide (420 mg, 2.94 mmol) and $K_2CO_3$ (15.1 g, 111 mmol). The mixture was refluxed for 9-12 hr until no more water was observed being collected in the Dean-Stark trap. The remaining toluene was then removed by distillation and the reaction mixture was cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by addition of 200 mL of 10% NaOH solution. The mixture was then extracted with ether (2×100 mL) to remove impurities and the water layer was made acidic by the addition of 100 mL of 2 M HCl solution. The aqueous solution was again extracted with ether (2×100 mL) and the ether layers were combined. Carbon black (2 g) was added and the ether was filtered through a short plug of silica gel to remove any insoluble components. The solvent was removed and the oil was vacuum dried to yield the analytically pure 2:1 hydroxy terminated oligomer (12.5 g, 90%) as an amber solid.

EXAMPLE 10

Synthesis of 2:1 oligomeric vinyl silane terminated resin based on bisphenol A6F and 1,3-dibromobenzene—To a 100 mL three-necked flask fitted with a thermometer, a Dean-Stark trap with condenser, and a nitrogen inlet were added the 2:1 bisphenol A6F/1,3-dibromobenzene based hydroxyl terminated aromatic ether oligomer (10.0 g, 13.4 mmol), triethylamine (4.01 ml, 28.8 mmol), and anhydrous tetrahydrofuran (100 mL). The reaction mixture was cooled by means of an ice bath and vinyl(dimethylchloro)silane (3.98 ml, 28.1 mmol) was added dropwise. The resulting mixture was stirred for 1 h. The mixture was poured into water and extracted with diethyl ether. The solvent was removed in vacuo and the resulting oil dissolved in 1:1 methylene chloride:hexane was filtered through a silica plug. The solvent was removed in vacuo and the clear oil was vacuum dried to yield the 2:1 oligomeric vinyl silane terminated resin (11.5 g, 94%). IR [cm$^{-1}$]: δ 3053 (C=CH), 2969 (CH$_3$), 1588 (C=C), 1500 (aromatic), 1245 (C—O), 1170 (C—O), 834 (aromatic).

EXAMPLE 11

Catalytic hydrosilylation reaction with 2:1 oligomeric vinyl silane terminated resin based on bisphenol A6F and 1,3-dibromobenzene and tetrakis(dimethylsiloxy)silane (3:1 ratio)—A mixture formulated from the 2:1 oligomeric vinyl silane terminated resin (0.44 g) of Example 10 and tetrakis (dimethylsiloxy)silane (0.05 mL) was dissolved in 1 mL of dry toluene. While stirring, 8 µL of 2-2.5% platinum-vinyl-methylsiloxane complex in xylene solution was added. The mixture was transferred to a silicone mold and was allowed to gel at room temperature (4 h). The sample was post cured above 100° C. to completely cure the resin. The result was a transparent elastomeric sample, which had good thermal and oxidative stability and retained >40% weight after heating under air to 1000° C.

EXAMPLE 12

Catalytic hydrosilylation reaction with 2:1 oligomeric vinyl silane terminated resin based on bisphenol A6F and 1,3-dibromobenzene and phenyl tris(dimethylsiloxy)silane (1:1 ratio)—A mixture formulated from the 2:1 oligomeric vinyl silane terminated resin (0.20 g) of Example 10 and phenyl tris(dimethylsiloxy)silane (0.09 mL) was dissolved in 1 mL of dry toluene. While stirring, 20 µL of 2-2.5% platinum-vinylmethylsiloxane complex in xylene solution was added. The mixture was transferred to a silicone mold and allowed to gel at room temperature (3 h). The sample was post cured above 100° C. to completely cure the resin. The result was a transparent elastomeric sample, which had good thermal and oxidative stability and retained >40% weight after heating under air to 1000° C.

EXAMPLE 13

Catalytic hydrosilylation reaction with 2:1 oligomeric vinyl silane terminated resin based on bisphenol A6F and 1,3-dibromobenzene and methyl tris(dimethylsiloxy)silane (2:1 ratio)—A mixture formulated from the 2:1 oligomeric vinyl silane terminated resin (0.35 g) of Example 10 and methyl tris(dimethylsiloxy)silane (0.045 mL) was dissolved in 1 mL of dry toluene. While stirring, 20 µL of 2-2.5% platinum-vinylmethylsiloxane complex in xylene solution was added. The mixture was transferred to a silicone mold and allowed to gel at room temperature (2 h). The sample was post cured above 100° C. to completely cure the resin. The result was a transparent elastomeric sample, which had good thermal and oxidative stability and retained >40% weight after heating under air to 1000° C.

EXAMPLE 14

Catalytic hydrosilylation reaction with 2:1 oligomeric vinyl silane terminated resin based on bisphenol A6F and 1,3-dibromobenzene and hydride terminated polydimethylsiloxane (1:2 ratio, rapid cure)—A mixture formulated from the 2:1 oligomeric vinyl silane terminated resin (0.20 g) of Example 10 and hydride terminated polydimethylsiloxane (m.w. ~450 g/mol) (0.18 g) was dissolved in 1 mL of dry toluene. While stirring, a rapid cure catalyst (25 µL of a 2-2.5% platinum-vinylmethylsiloxane complex in xylene solution) was added. The mixture was transferred to a silicone mold and allowed to gel at room temperature (12 h). The sample was post cured above 100° C. to completely cure the resin. The result was a transparent elastomeric sample, which had good thermal and oxidative stability, retained >40% weight after heating under air to 1000° C., and exhibited a glass transition temperature below 0° C.

EXAMPLE 15

Synthesis of resorcinol based hydroxy terminated oligomer (2:1)—To a 100 mL three-neck flask fitted with a thermometer, a Dean-Stark trap with condenser, and nitrogen inlet was added resorcinol (1,3-dihydroxybenzene) (20.0 g, 181 mmol), 1,3-dibromobenzene (11.0 mL, 21.42 g, 90.8 mmol), 1,10-phenanthroline (700 mg, 6.36 mmol), and N,N-dimethylformamide (80 mL). The resulting mixture was degassed with nitrogen for 10 min followed by the addition of copper (I) bromide (540 mg, 3.76 mmol) and $K_2CO_3$ (62.7 g, 454 mmol). The mixture was refluxed for 9-12 hr until no more water was observed being collected in the Dean-Stark trap. The remaining toluene was then removed by distillation and the reaction mixture was cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by the addition of 200 mL of 10% NaOH solution. The mixture was extracted with ether (2×100 mL) to remove impurities and the water layer was made acidic by the addition of 100 mL of 2 M HCl solution. The water was again extracted with ether (2×100 mL) and the ether layers were combined. Carbon black (2 g) was added and the ether was filtered through a short plug of silica gel to remove any insoluble components. The solvent was removed and the oil vacuum was dried to yield the analytically pure 2:1 hydroxy terminated oligomer (19.6 g, 74%) as a red oil.

EXAMPLE 16

Synthesis of 2:1 oligomeric vinyl silane terminated resin based on resorcinol and 1,3-dibromobenzene—To a 100 mL three-necked flask fitted with a thermometer, a Dean-Stark trap with condenser, and a nitrogen inlet were added the 2:1 resorcinol/1,3-dibromobenzene based hydroxyl terminated aromatic ether oligomer (10.0 g, 33.8 mmol), triethylamine (10.1 ml, 74.8 mmol), and anhydrous tetrahydrofuran (200 mL). The reaction mixture was cooled by means of an ice bath and vinyl(dimethylchloro)silane (10.1 ml, 71.4 mmol) was added dropwise. The resulting mixture was stirred for 1 h. The mixture was poured into water and extracted with diethyl ether. The solvent was removed in vacuo and the resulting oil was dissolved in 1:1 methylene chloride:hexane and filtered through a silica plug. The solvent was removed in vacuo and the clear oil was vacuum dried to yield the 2:1 oligomeric vinyl silane terminated resin (14.2 g, 90%). IR [$cm^{-1}$]: δ 3052 (C=CH), 2975 ($CH_3$), 1593 (C=C), 1503 (aromatic), 1241 (C—O), 1171 (C—O), 832 (aromatic).

EXAMPLE 17

Catalytic hydrosilylation reaction with 2:1 oligomeric vinyl silane terminated resin based on resorcinol and 1,3-dibromobenzene and tetrakis(dimethylsiloxy)silane (2.5:1 ratio)—A mixture formulated from the 2:1 oligomeric vinyl silane terminated resin (0.42 g) of Example 16 and tetrakis (dimethylsiloxy)silane (0.14 mL) was dissolved in 2 mL of dry toluene. While stirring, 25 μL of a 2-2.5% platinum-vinylmethylsiloxane complex in xylene solution was added. The mixture was transferred to a silicone mold and allowed to gel at room temperature (3 h). The sample was post cured above 100° C. to completely cure the resin. The result was a transparent elastomeric sample, which had good thermal and oxidative stability and retained >40% weight after heating under air to 1000° C.

EXAMPLE 18

Formulation of carbon nanotubes with a catalytic hydrosilylation reaction of 2:1 oligomeric vinyl silane terminated resin based on bisphenol A and 1,3-dibromobenzene and tetrakis(dimethylsiloxy)silane (2:1 ratio)—A mixture formulated from the 2:1 oligomeric vinyl silane terminated resin (0.40 g) of Example 2 and tetrakis(dimethylsiloxy)silane (0.09 mL) was dissolved in 1 mL of dry toluene and various amounts of carbon nanotubes (0.01 to 20 weight %) were added with stirring. With continued stirring, 10 μL of 2-2.5% platinum-vinylmethylsiloxane complex in xylene solution was added. The mixture was transferred to a silicone mold and allowed to gel at room temperature overnight. The sample was post cured above 100° C. to completely cure the resin. The result was an opaque elastomeric sample, which had good thermal and oxidative stability and retained >40% weight after heating under air to 1000° C.

EXAMPLE 19

Formulation of clay with a catalytic hydrosilylation reaction of 2:1 oligomeric vinyl silane terminated resin based on bisphenol A and 1,3-dibromobenzene and tetrakis(dimethylsiloxy)silane (2:1 ratio)—A mixture formulated from the 2:1 oligomeric vinyl silane terminated resin (0.40 g) of Example 2 and tetrakis(dimethylsiloxy)silane (0.09 mL) was dissolved in 1 mL of dry toluene and various amount of clay (hydrated aluminum silicate; 0.01 to 20 weight %) were added with stirring. With continued stirring, 25 μL of 2-2.5% platinum-vinylmethylsiloxane complex in xylene solution was added. The mixture was transferred to a silicone mold and allowed to gel at room temperature overnight. The sample was post cured above 100° C. to completely cure the resin. The result was an opaque elastomeric sample, which had good thermal and oxidative stability and retained >40% weight after heating under air to 1000° C.

EXAMPLE 20

Formulation of carbon nanofibers with a catalytic hydrosilylation reaction of 2:1 oligomeric vinyl silane terminated resin based on bisphenol A and 1,3-dibromobenzene and tetrakis(dimethylsiloxy)silane (2:1 ratio)—A mixture formulated from the 2:1 oligomeric vinyl silane terminated resin (0.45 g) of Example 2 and tetrakis(dimethylsiloxy)silane (0.10 mL) was dissolved in 1 mL of dry toluene and various amounts of carbon nanofibers (0.01 to 20 weight %) were added with stirring. With continued stirring, 15 μL of 2-2.5% platinum-vinylmethylsiloxane complex in xylene solution was added. The mixture was transferred to a silicone mold and allowed to gel at room temperature overnight. The sample was post cured above 100° C. to completely cure the resin. The result was an opaque elastomeric sample, which had good thermal and oxidative stability and retained >40% weight after heating under air to 1000° C.

EXAMPLE 21

Formulation of a metal oxide with a catalytic hydrosilylation reaction of 2:1 oligomeric vinyl silane terminated resin based on bisphenol A and 1,3-dibromobenzene and tetrakis (dimethylsiloxy)silane (2:1 ratio)—A mixture formulated from the 2:1 oligomeric vinyl silane terminated resin (0.38 g) of Example 2 and tetrakis(dimethylsiloxy)silane (0.08 mL) was dissolved in 1 mL of dry toluene and various amount of powdered antimony oxide (0.01 to 20 weight %) were added with stirring. With continued stirring, 20 µL of 2-2.5% platinum-vinylmethylsiloxane complex in xylene solution was added. The mixture was transferred to a silicone mold and allowed to gel at room temperature (12 h). The sample was post cured above 100° C. to completely cure the resin. The result was an opaque elastomeric sample, which had good thermal and oxidative stability and retained >40% weight after heating under air to 1000° C.

EXAMPLE 22

Formulation of microballoons with a catalytic hydrosilylation reaction of 2:1 oligomeric vinyl silane terminated resin based on bisphenol A and 1,3-dibromobenzene and tetrakis(dimethylsiloxy)silane (2:1 ratio)—A mixture formulated from the 2:1 oligomeric vinyl silane terminated resin (0.50 g) of Example 2 and tetrakis(dimethylsiloxy)silane (0.12 mL) was dissolved in 1 mL of dry toluene and various amount of microballoons (0.01 to 20 weight %) were added with stirring. With continued stirring, 50 µL of 2-2.5% platinum-vinylmethylsiloxane complex in xylene solution was added. The mixture was transferred to a silicone mold and allowed to gel at room temperature (10 h). The sample was post cured above 100° C. to completely cure the resin. The result was an opaque elastomeric sample, which had good thermal and oxidative stability and retained >40% weight after heating under air to 1000° C. and was less dense than Example 2.

EXAMPLE 23

Synthesis of 2:1 hydroxy terminated oligomer based on 1,3-dibromobenzene (excess) and bisphenol A6F—To a 100 mL three neck flask fitted with a thermometer, a Dean-Stark trap with condenser, and nitrogen inlet were added bisphenol A6F (3.67 g, 11.0 mmol), 1,3-dibromobenzene (2.64 mL, 5.16 g, 21.9 mmol), 1,10-phenanthroline (350 mg, 1.94 mmol), and N,N-dimethylformamide (50 mL). The resulting mixture was degassed with nitrogen for 10 min, followed by the addition of copper (1) bromide (420 mg, 2.94 mmol) and $K_2CO_3$ (7.80 g, 23.9 mmol). The mixture was refluxed for 9-12 hr until no more water was observed being collected in the Dean-Stark trap. The remaining toluene was then removed by distillation and the reaction mixture was cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by addition of 200 mL of 10% NaOH solution. The mixture was then extracted with ether (2×100 mL) to remove impurities and the water layer was made acidic by the addition of 100 mL of 2 M HCl solution. The aqueous solution was again extracted with ether (2×100 mL) and the ether layers were combined. Carbon black (2 g) was added and the ether was filtered through a short plug of silica gel to remove any insoluble components. The solvent was removed and the oil was vacuum dried to yield the analytically pure 2:1 hydroxy terminated oligomer (6.35 g, 90%) as an amber solid.

EXAMPLE 24

Synthesis of 2:1 oligomeric vinyl silane terminated resin based on 1,3-dibromobenzene (excess) and bisphenol A6F—

To a 100 mL three-necked flask fitted with a thermometer, a Dean-Stark trap with condenser, and a nitrogen inlet were added the oligomeric product from the reaction of 1,3-dibromobenzene (2.81 g, 11.9 mmol), bisphenol A6F (2.00 g, 3.1 mmol), and Mg metal (0.166 g, 6.82 mmol) in 25 mL of dry tetrahydrofuran. The mixture was heated to reflux for 1 h and then cooled to 0° C. Vinyl(dimethylchloro)silane (0.92 ml, 6.5 mmol) was then added dropwise. The mixture was cooled, poured into water, and extracted with diethyl ether. The solvent was removed in vacuo and the resulting oil was dissolved in 1:1 methylene chloride:hexane and filtered through a silica plug. The solvent was removed in vacuo and the clear oil was vacuum dried to yield the 2:1 oligomeric vinyl silane terminated resin (1.82 g, 90%). IR [$cm^{-1}$]: δ 3060 (C=CH), 2970 ($CH_3$), 1594 (C=C), 1498 (aromatic), 1243 (C—O), 1171 (C—O), 833 (aromatic).

EXAMPLE 25

Catalytic hydrosilylation reaction with 2:1 oligomeric vinyl silane terminated resin based on 1,3-dibromobenzene (excess) and bisphenol A6F and tetrakis(dimethylsiloxy)silane (2:1 ratio)—A mixture of 0.30 g of vinyl terminated oligomeric monomer from Example 24 and tetrakis(dimethylsiloxy)silane (0.05 mL) was dissolved in 1 mL of dry toluene. While stirring, 30 µL of 2-2.5% platinum-vinylmethylsiloxane complex in xylene solution was added. The mixture was transferred to a silicone mold and allowed to gel at room temperature overnight. The sample was post cured above 100° C. to completely cure the resin. The result was a transparent elastomeric sample, which had good thermal and oxidative stability and retained >40% weight after heating under air to 1000° C.

EXAMPLE 26

Synthesis of 4:3 hydroxy terminated oligomer based on bisphenol A and 1,3-dibromobenzene—To a 100 mL three neck flask fitted with a thermometer, a Dean-Stark trap with condenser, and nitrogen inlet was added bisphenol A (10.0 g, 43.8 mmol), 1,3-dibromobenzene (7.76 g, 32.9 mmol), 1,10-phenanthroline (350 mg, 1.94 mmol), and N,N-dimethylformamide (50 mL). The resulting mixture was degassed with nitrogen for 10 min, followed by the addition of copper (I) bromide (420 mg, 2.94 mmol) and $Cs_2CO_3$ (7.80 g, 23.9 mmol). After filling the Dean-Stark trap with toluene and adding 5 mL to the reaction flask, the mixture was heated to reflux at 145° C. for 1 hr. The water formed in the reaction was removed by azeotropic distillation and at this time an additional portion of $K_2CO_3$ (15.1 g, 111 mmol) was added. The mixture was refluxed for 9-12 hr until no more water was observed being collected in the Dean-Stark trap. The remaining toluene was then removed by distillation and the reaction mixture cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by addition of 200 mL of 10% NaOH solution. The mixture was then extracted with ether (2×100 mL) to remove impurities and the water layer was made acidic by the addition of 100 mL of 2 M HCl solution. The aqueous solution was again extracted with ether (2×100 mL) and the ether layers were combined. Carbon black (2 g) was added and the ether filtered through a short plug of silica gel to remove any insoluble components. The solvent was removed and the oil was vacuum dried to yield the analytically pure 2:1 hydroxy terminated oligomer (10.1 g, 90%) as an amber solid.

EXAMPLE 27

Synthesis of 2:1 oligomeric vinyl silane terminated resin based on bisphenol A and 1,3-dibromobenzene—To a 100 mL three-necked flask fitted with a thermometer, a Dean-Stark trap with condenser, and a nitrogen inlet were added the 4:3 bisphenol A/1,3-dibromobenzene based hydroxyl terminated aromatic ether oligomer (2.00 g, 3.77 mmol), triethylamine (0.59 ml, 4.2 mmol), and anhydrous tetrahydrofuran (25 mL). The reaction mixture was cooled by means of an ice bath and vinyl(dimethylchloro)silane (0.57 mL, 4.00 mmol) added dropwise. The resulting mixture was stirred for 1 h. The mixture was poured into water and extracted with diethyl ether. The solvent was removed in vacuo and the resulting oil was dissolved in 1:1 methylene chloride:hexane and filtered through a silica plug. The solvent was removed in vacuo and the clear oil was vacuum dried to yield the 2:1 oligomeric vinyl silane terminated resin (2.21 g, 95%). IR [cm$^{-1}$]: δ 3052 (C=CH), 2967 (CH$_3$), 1593 (C=C), 1500 (aromatic), 1242 (C—O), 1171 (C—O), 834 (aromatic).

EXAMPLE 28

Catalytic hydrosilylation reaction with 2:1 oligomeric vinyl silane terminated resin based on bisphenol A and 1,3-dibromobenzene and tetrakis(dimethylsiloxy)silane (2:1 ratio)—A mixture formulated from the 4:3 oligomeric vinyl silane terminated resin (0.40 g) of Example 27 and tetrakis (dimethylsiloxy)silane (0.08 mL) was dissolved in 1 mL of dry toluene. While stirring, 10 μL of 2-2.5% platinum-vinylmethylsiloxane complex in xylene solution was added. The mixture was transferred to a silicone mold and was allowed to gel at room temperature (8 h). The sample was post cured above 100° C. to completely cure the resin. The result was a transparent elastomeric sample, which had good thermal and oxidative stability and retained >40% weight after heating under air to 1000° C.

EXAMPLE 29

Synthesis of 3:2 hydroxy terminated oligomer based on 1,3-dibromobenzene (excess) and bisphenol A—To a 100 mL three neck flask fitted with a thermometer, a Dean-Stark trap with condenser, and nitrogen inlet were added bisphenol A (4.00 g, 11.0 mmol), 1,3-dibromobenzene (6.21 g, 26.3 mmol), 1,10-phenanthroline (350 mg, 1.94 mmol), and N,N-dimethylformamide (50 mL). The resulting mixture was degassed with nitrogen for 10 min, followed by the addition of copper (I) bromide (420 mg, 2.94 mmol) and K$_2$CO$_3$ (7.80 g, 23.9 mmol). The mixture was refluxed for 9-12 hr until no more water was observed being collected in the Dean-Stark trap. The remaining toluene was then removed by distillation and the reaction mixture was cooled to ambient temperature. Water was added (500 mL) to the reaction mixture. At this point, the mixture was slightly basic and 2 M HCl (300 mL) was added. The mixture was then extracted with ether (2×100 mL) and the combined ether layers were washed with 2 M HCl (1×100 mL) and water (1×100 mL). The hydroxy terminated oligomeric intermediate was extracted into the water layer by addition of 200 mL of 10% NaOH solution. The mixture was then extracted with ether (2×100 mL) to remove impurities and the water layer was made acidic by the addition of 100 mL of 2 M HCl solution. The aqueous solution was again extracted with ether (2×100 mL) and the ether layers were combined. Carbon black (2 g) was added and the ether was filtered through a short plug of silica gel to remove any insoluble components. The solvent was removed and the oil was vacuum dried to yield the analytically pure 2:1 hydroxy terminated oligomer (5.67 g, 95%) as an amber solid.

EXAMPLE 30

Synthesis of 3:2 oligomeric vinyl silane terminated resin based on 1,3-dibromobenzene (excess) and bisphenol A—To a 100 mL three-necked flask fitted with a thermometer, a Dean-Stark trap with condenser, and a nitrogen inlet were added the 3:2 oligomer based on 1,3-dibromobenzene (excess) and bisphenol A (2.00 g) from Example 29 and Mg metal (0.13 g, 6.82 mmol) in 25 mL of dry tetrahydrofuran. The mixture was heated to reflux for 1 h and then cooled to 0° C. Vinyl(dimethylchloro)silane (0.70 ml, 5.0 mmol) was then added dropwise. The mixture was cooled, poured into water, and extracted with diethyl ether. The solvent was removed in vacuo and the resulting oil was dissolved in 1:1 methylene chloride:hexane and filtered through a silica plug. The solvent was removed in vacuo and the clear oil was vacuum dried to yield the 2:1 oligomeric vinyl silane terminated resin (1.86 g, 92%). IR [cm$^{-1}$]: δ 3060 (C=CH), 2970 (CH$_3$), 1594 (C=C), 1498 (aromatic), 1243 (C—O), 1171 (C—O), 833 (aromatic)

EXAMPLE 31

Catalytic hydrosilylation reaction with 3:2 oligomeric vinyl silane terminated resin based on 1,3-dibromobenzene (excess) and bisphenol A and tetrakis(dimethylsiloxy)silane (2:1 ratio)—A mixture of 0.50 g of vinyl terminated oligomeric monomer from Example 30 and tetrakis(dimethylsiloxy)silane (0.05 mL) was dissolved in 1 mL of dry toluene. While stirring, 25 μL of 2-2.5% platinum-vinylmethylsiloxane complex in xylene solution was added. The mixture was transferred to a silicone mold and allowed to gel at room temperature overnight. The sample was post cured above 100° C. to completely cure the resin. The result was a transparent elastomeric sample, which had good thermal and oxidative stability and retained >40% weight after heating under air to 1000° C.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. An oligomer having the formula:

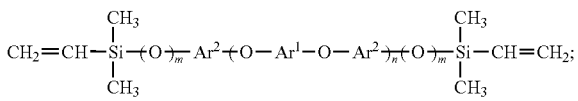

wherein Ar$^1$ and Ar$^2$ are each selected from an aromatic group and a bisphenol residue;

wherein at least one of Ar$^1$ and Ar$^2$ is the aromatic group;

wherein m is zero or one; and wherein n is a positive integer.

2. The oligomer of claim 1, wherein the aromatic group is phenylene.

3. The oligomer of claim 1, wherein n is 1.

4. The oligomer of claim 1, wherein the oligomer has the formula:

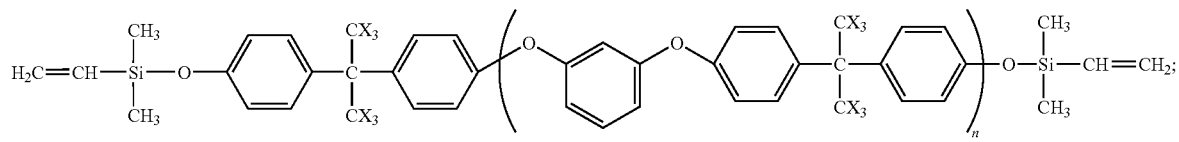

wherein X is H or F.

5. The oligomer of claim 1, wherein the oligomer has the formula:

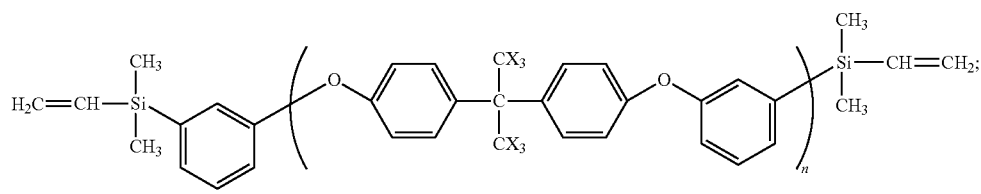

wherein X is H or F.

6. The oligomer of claim 1, wherein the oligomer has the formula:

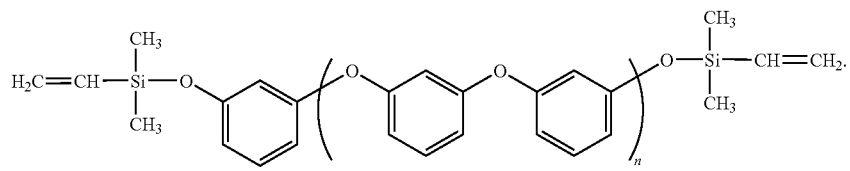

7. A polymer made by reacting an oligomer having the formula:

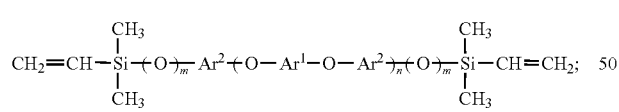

wherein $Ar^1$ and $Ar^2$ are each selected from an aromatic group and a bisphenol residue;

wherein at least one of $Ar^1$ and $Ar^2$ is the aromatic group;

wherein m is zero or one; and wherein n is a positive integer;

with a crosslinker having at least two silyl hydrogen atoms.

8. The polymer of claim 7, wherein the aromatic group is phenylene.

9. The polymer of claim 7, wherein n is 1.

10. The polymer of claim 7, wherein the oligomer has the formula:

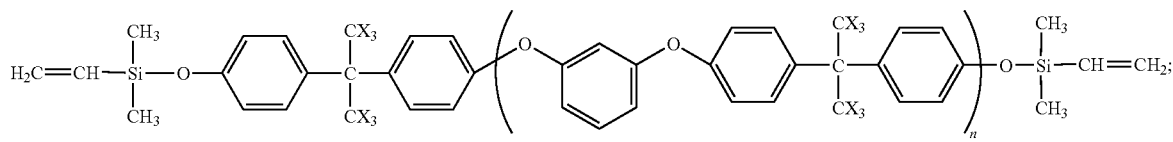

wherein X is H or F.

11. The polymer of claim 7, wherein the oligomer has the formula:

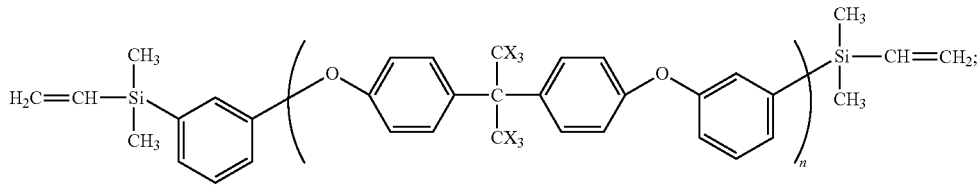

wherein X is H or F.

12. The polymer of claim 7, wherein the oligomer has the formula:

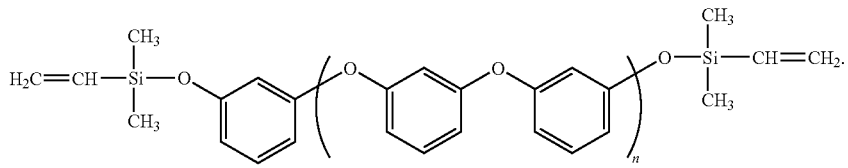

13. The polymer of claim 7, wherein the crosslinker is tetrakis(dimethylsiloxy)silane, bis[(p-dimethylsilyl)phenyl] ether, diphenylsilane, 1,1,3,3,5,5,7,7-octamethyltetrasiloxane, 1,1,3,3-tetramethyldisiloxane, phenyl tris(dimethylsiloxy)silane, methyl tris(dimethylsiloxy)silane, or a hydride terminated polydimethylsiloxane.

14. A composite comprising:
 the polymer of claim 7; and
 carbon nanotubes, a clay, carbon nanofibers, a metal oxide, or microballoons.

15. A method comprising:
 reacting a compound having the formula:

$$T-Ar^2-\!\!\left(O-Ar^1-O-Ar^2\right)_{\!n}\!\!-T;$$

wherein T is —OH, —Br, or —I;
 wherein $Ar^1$ and $Ar^2$ are each selected from an aromatic group and a bisphenol residue;
 wherein at least one of $Ar^1$ and $Ar^2$ is the aromatic group; and
 wherein n is a positive integer;
 with vinyl(dimethylchloro)silane to form an oligomer having the formula:

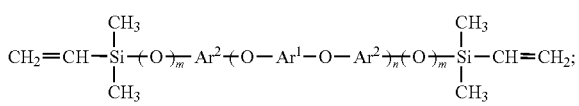

wherein m is zero or one.

16. The method of claim 15, wherein the aromatic group is phenylene.

17. The method of claim 15, wherein n is 1.

18. The method of claim 15, wherein the compound has the formula:

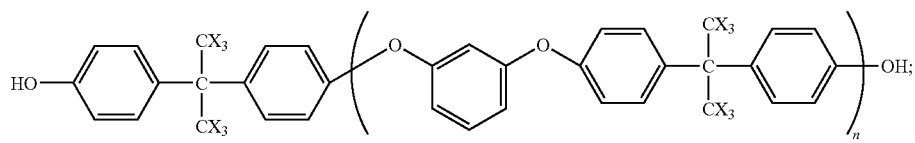

wherein X is H or F.

19. The method of claim 15, wherein the compound has the formula:

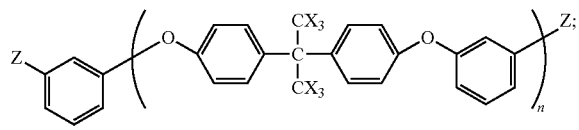

wherein Z is —Br or —I.
wherein X is H or F.

20. The method of claim 15, wherein the compound has the formula:

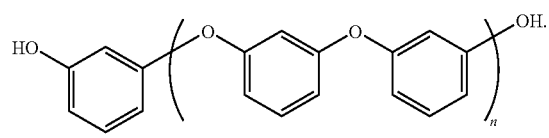

21. The method of claim 15, further comprising:
reacting a dibromobenzene or a diiodobenzene with a bisphenol or a dihydroxybenzene to form the compound.

22. The method of claim 15, further comprising:
reacting the oligomer with a crosslinker having at least two silyl hydrogen atoms.

23. The method of claim 22, wherein the crosslinker is tetrakis(dimethylsiloxy)silane, bis[(p-dimethylsilyl)phenyl] ether, diphenylsilane, 1,1,3,3,5,5,7,7-octamethyltetrasiloxane, 1,1,3,3-tetramethyldisiloxane, phenyl tris(dimethylsiloxy)silane, methyl tris(dimethylsiloxy)silane, or a hydride terminated polydimethylsiloxane.

24. The method of claim 22, wherein reacting the oligomer with the crosslinker occurs in the presence of carbon nanotubes, a clay, carbon nanofibers, a metal oxide, or microballoons.

* * * * *